United States Patent [19]
Antons et al.

[11] Patent Number: 5,872,283
[45] Date of Patent: Feb. 16, 1999

[54] PROCESS FOR DECARBOXYLATION OF HALOGENATED AROMATIC CARBOXYLIC ACIDS

[75] Inventors: Stefan Antons, Leverkusen; Guido Steffan, Odenthal; Helmut Fiege, Leverkusen, all of Germany

[73] Assignee: Bayer Aktiengesellschaft, Leverkusen, Germany

[21] Appl. No.: 883,267

[22] Filed: Jun. 26, 1997

[30] Foreign Application Priority Data

Jul. 9, 1996 [DE] Germany .................. 196 27 411.7

[51] Int. Cl.⁶ .................. C07C 63/70; C07C 51/38
[52] U.S. Cl. .................................................. 562/479
[58] Field of Search .................. 562/479, 484; 570/127

[56] References Cited

U.S. PATENT DOCUMENTS

| | | | |
|---|---|---|---|
| 4,755,621 | 7/1988 | Kysela et al. | 562/411 |
| 4,782,180 | 11/1988 | Wemple et al. | 562/479 |
| 4,791,225 | 12/1988 | Irikura et al. | 562/493 |
| 4,822,912 | 4/1989 | Naumann et al. | 562/493 |
| 5,072,038 | 12/1991 | Klauke et al. | 562/840 |
| 5,648,504 | 7/1997 | Seki et al. | 549/246 |

FOREIGN PATENT DOCUMENTS

| | | |
|---|---|---|
| 0 194 671 B1 | 9/1986 | European Pat. Off. . |
| 0218111 | 4/1987 | European Pat. Off. . |
| HU 195 176 | 4/1988 | Hungary . |
| HU 196 194 | 10/1988 | Hungary . |
| HU 196 735 | 1/1989 | Hungary . |
| 61043130 | 3/1986 | Japan . |
| 6425737 | 1/1989 | Japan . |
| 5190758 | 1/1995 | Japan . |
| 2122190 | 1/1984 | United Kingdom . |

OTHER PUBLICATIONS

Patent Abstracts of Japan, vol. 095, No. 004, May 31, 1995 JP 07 017904 (Asahi Glass Co. Ltd.).

*Primary Examiner*—Richard L. Raymond
*Assistant Examiner*—Deepak R. Rao
*Attorney, Agent, or Firm*—Sprung Kramer Schaefer & Briscoe

[57] ABSTRACT

Halogenated aromatic carboxylic acids are decarboxylated by heating them in the presence of water at temperatures of 80° to 180° C. and in the presence of water and other acids at temperatures above 80° C.

16 Claims, No Drawings

PROCESS FOR DECARBOXYLATION OF HALOGENATED AROMATIC CARBOXYLIC ACIDS

The present invention relates to a particularly simple process for the decarboxylation of halogenated aromatic carboxylic acids, in particular for the preparation of 2,3,5, 6-tetrafluorobenzoic acid by decarboxylation of 2,3,5,6-tetrafluoroterephthalic acid.

Some processes for the decarboxylation of halogenated aromatic carboxylic acids are already disclosed, thus, GB-A 2 122 190 describes the decarboxylation of 2,3,5,6-tetrafluoroterephthalic acid in polar aprotic solvents. However, the reaction proceeds unselectively and principally produces the completely decarboxylated product 1,2, 4,5-tetrafluorobenzene, without tetrafluorobenzoic acid being able to be isolated.

According to JP 64-25 737, the decarboxylation of halogenated aromatic carboxylic acids is carried out in the presence of tertiary amines. However, this requires a complex work-up, in which the reaction mixture is first treated with sodium hydroxide solution, then the tertiary amine is separated off and recycled and, finally, the product is isolated by acidification.

EP-A 218 111 proposes carrying out this decarboxylation in the presence of tertiary amines, additionally in the presence of a polar aprotic solvent. This makes the process still more complicated.

JP 5/190 758 describes the preparation of 3,4,5,6-tetrafluorobenzoic acid by heating an aqueous solution of 3,4,5,6-tetrafluoroisophthalic acid to 190° C. (see Example 7). Example 8 describes this reaction in tri-(n-butylamine) and a better yield is obtained at lower reaction temperature. This thus confirms the impression already existing from the other prior art that addition of bases is particularly advantageous.

Finally, JP 61/43 130 describes the complete decarboxylation of 3,4,5,6-tetrafluorophthalic acid in aqueous medium to give 1,2,3,4-tetrafluorobenzene. The preparation of 2,3, 5,6-tetrafluorobenzoic acid is not described.

In particular in view of JP 61/43 130, it appears to be difficult to carry out the decarboxylation without addition of bases in such a manner that only one carboxyl group is selectively degraded. Furthermore, it appears to be improbable that the decarboxylation can be carried out in an aqueous acidic medium.

A process has now been found for the decarboxylation of halogenated aromatic carboxylic acids of the formula (I),

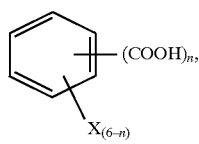

in which
X represents fluorine, chlorine and/or bromine and
n represents 1 or 2,
with the formation of compounds of the formula (II)

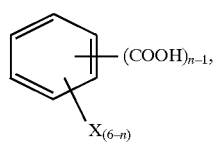

in which
X and n have the meaning specified in the formula (I),
which comprises heating a compound of the formula (I) together with water to temperatures of 80° to 180° C. or together with water and another acid to temperatures above 80° C.

In the formnulae (I) and (II), X located on an aromatic ring can be identical or different. Preferably, X represents fluorine and n represents 2.

Particularly preferably, 2,3,5,6-tetrafluoroterephthalic acid is used in the process according to the invention and 2,3,5,6-tetrafluorobenzoic acid is prepared.

The halogenated aromatic carboxylic acids of the formula (I) need not be used in pure form. They can also be used in water-containing form, if appropriate also in a form containing yet other acids. Since halogenated aromatic carboxylic acid of formula (I), in particular that where n=2, is frequently prepared by acidic saponification of the corresponding nitriles it is a great advantage of the process according to the invention that reaction mixtures from the acidic saponification of nitriles can be used directly. No measures are then required for the purification or work-up of such reaction mixtures from the acidic nitrile saponification.

For example, halogenated aromatic carboxylic acids of the formula (I) can be used which contain upto 90% by weight of water and, if appropriate, upto 60% by weight of other acids, the total content of water and other acid not exceeding 95% by weight. Preferably, they contain 2 to 25% by weight of water and, if appropriate, 1 to 20% by weight of other acids. The other acids can be, e.g. sulfuric acid, hydrochloric acid, phosphoric acid and/or a $C_2$ to $C_{10}$ carboxylic acid, for instance acetic acid. Preference is given to sulphuric acid, since the above specified acidic saponification of nitriles is customarily carried out with sulfuric acid. Obviously, halogenated aromatic carboxylic acids can alternatively be used which, in the scope of the technical possibilities, are free from water and/or other acids.

The process according to the invention can be carried out, e.g. in the presence of 0.5 to 15 times the amount by weight of water, based on the compound of the formula (I) used. Preferably, this amount is 0.8 to 6 times the amount by weight of water. If the compound of the formula (I) used does not contain sufficient water this must be added separately. In addition, the process according to the invention can be carried out, e.g. in the presence of upto 15 times the amount by weight of one or more other acids, based on the compound of the formula (I) used. Preferably, this amount is 0.01 to 5 times the amount by weight of one or more other acids. If the compound of the formula (I) used does not contain the desired amount of another acid, this must be added separately.

The compound of the formula (I) is heated together with water, preferably to a temperature of 90° to 170° C. and together with water and other acids to, for example, 80° to 200° C., preferably 90° to 180° C. If the reaction temperature at atmospheric pressure is above the boiling temperature of the reaction mixture, it is necessary to carry out the decarboxylation in a pressure-tight reactor, e.g. an autoclave.

The reaction times can be varied in a broad range and are, e.g. in the range from 1 to 60 hours. Generally, at higher reaction temperatures, shorter reaction times may be employed than at lower reaction temperatures. Lower reaction temperatures, e.g. those of 80° to 150° C., are advantageous if large amounts of water and relatively small amounts of other acids, or no other acids, are used.

Essential features of the process according to the invention are that it is carried out without addition of catalysts, bases and organic solvents.

The reaction mixture present after the decarboxylation according to the invention is carried out can be worked up, e.g. by cooling it, depressurizing it, filtering it and washing with water and drying the solid filtered off. In this manner, generally, products over 97% pure are obtained.

In view of the prior art described at the outset, in the process according to the invention, it is extremely surprising that, without addition of bases, and without organic solvents, carboxyl groups may be selectively eliminated successively with good yields from halogenated aromatic carboxylic acid and the decarboxylation products may be successively obtained in high purities. In addition, when there are two carboxyl groups present in the starting product, it is possible to eliminate only one selectively, in which case it is possible to operate particularly selectively, in particular in the presence of another acid.

Compounds of the formula (II), in particular 2,3,5,6-tetrafluorobenzoic acid, are valuable intermediates for the preparation of plant protection active compounds and pharmaceutical active compounds.

EXAMPLES

Example 1

80 g of 80% strength by weight 2,3,5,6-tetrafluoroterephthalic acid (containing 8% by weight of sulfuric acid and 12% by weight of water) were mixed with 300 g of water in a 0.6 l enamelled autoclave and heated for 40 hours at 130° C. After cooling to 20° C. and depressurizing, the suspension then present was filtered, washed with 60 g of water and the white solid was dried. 42 g of 2,3,5,6-tetrafluorobenzoic acid having a content of 98% by weight and a melting point of 151° C. were obtained.

Example 2

The procedure of Example 1 was followed, but instead of 300 g of water, only 200 g of water were added and the mixture was heated for 6 hours at 140° C. 47 g of 2,3,5,6-tetrafluorobenzoic acid having a content of 99.4% by weight were obtained.

Example 3

100 g of 2,3,5,6-tetrafluoroterephthalodinitrile were mixed with 140 ml of 70% strength by weight sulfuric acid in an enamelled autoclave and heated for 6 hours at 150° C. 260 ml of water were then added and the mixture was heated for 8 hours at 140° C. After the work-up of the reaction mixture, as specified in Example 1, 78.5 g of 99.5% strength by weight 2,3,5,6-tetrafluorobenzoic acid were obtained.

Example 4

The procedure of Example 3 was followed, but 246 g of 70% strength by weight sulfuric acid and, in addition, 50 g of glacial acetic acid were used, this mixture was heated for 5 hours at 170° C., then 440 ml of water were added and the mixture was heated for 10 hours at 160° C. After a work-up similar to Example 1, 96 g of 99.4% strength by weight 2,3,5,6-tetrafluorobenzoic acid were obtained.

Example 5 (for comparison—see JP 93/190 758)

20 g of 99.8% strength by weight 2,3,5,6-tetrafluoroterephthalic acid, which did not contain sulfuric acid, were heated with 60 g of water for 5 hours at 190° C. After cooling, an organic phase and an aqueous phase developed in the autoclave. The organic phase contained 62% of theory of 1,2,4,5-tetrafluorobenzene. The aqueous phase contained only traces of 2,3,5,6-tetrafluorobenzoic acid.

Example 6

750 ml of water and 80 g of 2,3,5,6-tetrafluoroterephthalic acid were placed at room temperature into an enamelled autoclave of 1.3 l capacity. The autoclave was then closed and heated for 21 hours at 130° C., with the pressure increasing to a maximum of 11.7 bar. The reaction mixture analyzed by HPLC contained 2,3,5,6-tetrafluorobenzoic acid in an amount which corresponded to 78.6% of theory.

We claim:

1. A process for the decarboxylation of halogenated aromatic carboxylic acids of the formula (I)

in which
X represents fluorine, chlorine and/or bromine and
n represents 2,
with the formation of compounds of the formula (II)

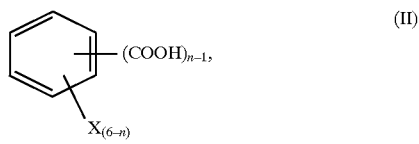

in which
X and n have the meaning specified in the formula (I), which comprises heating a compound of the formula (I) together with water to temperatures of 80° to 180° C. or together with water and another acid to temperatures above 80° C., wherein the compound of formula (I) is 2,3,5,6-tetrahaloterephthalic acid and the product prepared of formula (II) is 2,3,5,6-tetrahalobenzoic acid and further wherein the process is carried out without the addition of catalysts, bases and organic solvents.

2. The process as claimed in claim 1, wherein, in the formulae, X represents fluorine.

3. The process as claimed in claim 1, wherein 2,3,5,6-tetrafluoroterephthalic acid is used and 2,3,5,6-tetrafluorobenzoic acid is prepared.

4. The process as claimed in claim 1, wherein the halogenated aromatic carboxylic acid of the formula (I) is used in water-containing form.

5. The process as claimed in claim 1, wherein the halogenated aromatic formula (I) is used in a form containing yet other acids.

6. The process as claimed in claim 1, wherein the halogenated aromatic carboxylic acid of the formula (I) is used in the form of the reaction mixture which arises in the acidic saponification of the corresponding nitrites.

7. The process as claimed in claim 1, wherein it is carried out in the presence of 0.5 to 15 times the amount by weight of water, based on the compound of the formula (I) used.

8. The process as claimed in claim 1, wherein the compound of the formula (I) is heated together with water to temperatures of 90° to 170° C. and together with water and another acid to temperatures of 80° to 200° C.

9. The process as claimed in claim 1, wherein the reaction mixture present after the decarboxylation is worked up by cooling it, depressurizing it, filtering it and washing with water and drying the solid filtered off.

10. A process according to claim 1, wherein the another acid is selected from the group consisting of sulfuric acid, hydrochloric acid, phosphoric acid and/or $C_2$–$C_{10}$ carboxylic acid.

11. A process as recited in claim 1, wherein the another acid is sulfuric acid.

12. A process according to claim 1, wherein the compound of formula (I) is heated with 2–25% by weight water.

13. A process according to claim 1, wherein the compound of formula (I) is heated with water and up to 60% by weight of another acid.

14. A process according to claim 1, wherein the compound of formula (I) is heated with water and from 1–20% by weight of another acid.

15. A process according to claim 1, wherein the temperature of reaction with water ranges from 90°–170° C.

16. A process according to claim 1, wherein the temperature of reaction with water and another acid ranges from 90°–180° C.

* * * * *

UNITED STATES PATENT AND TRADEMARK OFFICE
CERTIFICATE OF CORRECTION

PATENT NO.   : 5,872,283
DATED        : February 16, 1999
INVENTOR(S)  : Antons, et al.

It is certified that error appears in the above-indentified patent and that said Letters Patent is hereby corrected as shown below:

Col. 2, line 15   Delete " nitrites " and substitute -- nitriles --

Col. 4, line 54   Delete " nitrites " and substitute -- nitrile --

Signed and Sealed this

Second Day of November, 1999

Attest:

Q. TODD DICKINSON

*Attesting Officer*    Acting Commissioner of Patents and Trademarks